United States Patent [19]
Jauregui
[11] Patent Number: 5,043,260
[45] Date of Patent: Aug. 27, 1991

[54] PERFUSION DEVICE WITH HEPATOCYTES

[75] Inventor: Hugo O. Jauregui, Providence, R.I.
[73] Assignee: Rhode Island Hospital, Providence, R.I.

[21] Appl. No.: 116,525
[22] Filed: Nov. 2, 1987
[51] Int. Cl.[5] .......................... C12N 5/08; C12M 3/00
[52] U.S. Cl. ................................ 435/1; 435/240.241; 435/240.242; 435/240.243; 435/284; 435/285; 435/311; 604/4
[58] Field of Search .................. 435/1, 284, 285, 311, 435/240.242, 240.241, 178, 181, 177, 269, 262, 240.243; 623/12; 436/827; 210/321.89, 645, 646; 604/4–6

[56] References Cited

U.S. PATENT DOCUMENTS

| | | | |
|---|---|---|---|
| 3,734,851 | 5/1973 | Matsumura . | |
| 4,853,324 | 8/1989 | Viles et al. | 435/283 |
| 4,869,826 | 9/1989 | Wang et al. | 210/679 |

OTHER PUBLICATIONS

Pharmacia Fine Chemicals, publication entitled, "*Affinity Chromatography*", 1983, pp. 52–61.
Wolf, C. F. W., and Munkelt, B. E., "Bilirubin Conjugation by an Artificial Liver Composed of Cultured Cells and Synthetic Capillaries", vol. XXI, *Trans. Amer. Soc. Artif. Int. Organs,* 1975, pp. 16–23.
Jauregui, H. O., et al., "Hybrid Artificial Liver", in Szycher, M. (ed.), *Biocompatible Polymers, Metals, and Other Composites* (Lancaster, Pa., Technomic Pub), 1983, pp. 907–928.
Jauregui, H. O., et al., "Adult Rat Hepatocyte Cultures as the Cellular Component of an Artificial Hybrid Liver", in Paul, J. P. (ed.), *Biomaterials in Artificial Organs,* (MacMillan), 1983, pp. 130–140.
Hager, J. C., et al., "Neonatal Hepatocyte Culture on Artificial Capillaries, A Model for Drug Metabolism and the Artificial Liver", *ASAIO J.,* 6:26–35, (Jan./Mar. 1983).
Steer, C. J., et al., "Studies on a Mammalian Hepatic Binding Protein Specific for Asialoglycoproteins", *Journal of Biological Chemistry,* vol. 255, No. 7. Apr. 10, 1980, pp. 3008–3113.
Curtis, A. S. G., et al., "Substrate Hydroxylation and Cell Adhesion", *J. Cell Science,* vol. 86, 1986, pp. 9–24.
Schnabel, W., *Polymer Degradation,* (Munich, 1981).
Hatten, M. E., and Francois, A. M., "Adhesive Specificity of Developing Cerebellar Cells on Lectin Substrata", *Developmental Biology,* vol. 87, 1981, pp. 102–113.
Seglen, P. O., "Preparation of Isolated Rat Liver Cells", Chapter 4, from *Methods in Cellular Biology,* 13:29–83, (1976).
McMillan, P. N., et al., "Light and Electron Microscope Analysis of Lectin Binding to Adult Rat Liver *in Situ*", *Laboratory Investigation,* vol. 50, No. 4, (1984), pp. 408–420.
Weigel, P. H., et al., "Specific Adhesion of Rat Hepatocytes to $\beta$-Galactosides Linked to Polyacrylamide Gels", *Journal of Biological Chemistry,* vol. 253, No. 2, Jan. 25, 1978, pp. 330–333.
Weigel, P. H., et al., "Adhesion of Hepatocytes to Immobilized Sugars", *Journal of Biological Chemistry,* vol. 254, No. 21, Nov. 10, 1979, pp. 10830–10838.

*Primary Examiner*—David L. Lacey
*Assistant Examiner*—William H. Beisner

[57] ABSTRACT

A perfusion device to grow and maintain hepatocytes including a chamber having a perfusion inlet and a perfusion outlet, a semipermeable membrane in the chamber defining separate perfusion and hepatocyte compartments, and hepatocytes in the hepatocyte compartment attached via oligosaccharide-lectin recognition linkage to a biopolymer support in the hepatocyte compartment.

49 Claims, 2 Drawing Sheets

N 42 38 44 5 46 40 W
W 40 5 12 42 N

PERFUSION DEVICE WITH HEPATOCYTES

FIELD OF THE INVENTION

The invention relates to perfusion devices incorporating hepatocytes, e.g., artificial external livers and hepatocyte reactors.

BACKGROUND OF THE INVENTION

The desirability of an artificial external liver, e.g., to be used with a patient with a deficient liver while awaiting a transplant, is known in the art, Jauregui, H. O., et al., "Hybrid Artificial Liver", in Szycher, M. (ed.), *Biocompatible Polymers, Metals, and Other Composites,* (Lancaster, PA, Technomic Pub) 1983, pp. 907–928; Matsumura U.S. Pat. No. 3,734,851.

Wolf, F. W., and Munkelt, B. E., "Bilirubin Conjugation by an Artificial Liver Composed of Cultured Cells and Synthetic Capillaries," Vol. XXI *Trans. Amer. Soc. Artif. Int. Organs,* 1975, pp. 16–23, describe experiments in which rat hepatoma (tumorous liver) cells were provided in the regions between hollow semipermeable fibers in a cartridge, and blood was passed through the fibers and treated by the hepatoma cells. In such hollow fiber devices, the fibers are used to isolate the cells from the patient's immune defense system and have pore sizes so as to permit transfer of toxic substances.

Hager, et al., "Neonatal Hepatocyte Culture on Artificial Capillaries. A Model for Drug Metabolism and the Artificial Liver", ASAIO J., 6:26–35 (Jan/Mar 1983), and Jauregui, H. O., et al., "Adult Rat Hepatocyte Cultures as the Cellular Component of an Artificial Hybrid Liver", in Paul, J. (ed.), *Biomaterials in Artificial Organs,* (MacMillan) 1983, pp. 130–140, describe experiments in which hepatocytes (healthy liver cells) were grown on external surfaces of and into walls of hollow, semipermeable fibers in a cartridqe. The latter reference suggests treating the fibers with collagen prior to seeding with hepatocytes to improve attachment.

Jauregui, H. O., et al., "Hybrid Artifical Liver", supra, discloses the desirability of attaching hepatocytes (which are anchorage dependent cells) to a biocompatible polymeric substrate (p. 913) and reports attaching using ligands such as asialoglycoprotein, insulin, epidermal growth factor, collagen, and fibronectin (p. 917).

SUMMARY OF THE INVENTION

The invention features in general a perfusion device that includes a porous membrane to separate a perfusion compartment from a hepatocyte compartment and employs oligosaccharide lectin recognition linkage to attach hepatocytes to a biopolymer support member in the hepatocyte compartment.

In preferred embodiments the hepatocytes have cytochrome P450 activity, which is the main detoxification activity of the liver cell; the membrane is provided by hollow fibers communicating with perfusion inlets and outlets of the device, and the hepatocytes are attached on exterior surface portions of the fibers; the lectins are Lens culinaris agglutinin (LCA), Phaseolus vulgaris agglutinin (PHA), or wheat germ agglutinin (WGA); the device also includes a waste inlet and a waste outlet, and there is a second set of hollow fibers communicating the waste inlet and outlet; there are two types of lectins connected to the two sets of fibers, the first type (LCA and PHA) recognizing sugars located predominantly at the blood sinusoidal domain of the hepatocytes, e.g., α-D-mannosyl and α-D-glucosyl (for LCA), β-D-galactosyl-(1-3)-NAc-galactosyl-β-D-galactosyl (for PHA), the second type (WGA) recognizing sugars located predominantly at the bile domain of the hepatocytes, e.g., β-NAc-neuraminic acid.

The perfusion device according to the invention can be used as a hepatocyte reactor. It can also be connected to a patient via venipuncture needles and used as an artificial liver.

Other advantages and features of the invention will be apparent from the following description of the preferred embodiments thereof and from the claims.

Description of Preferred Embodiments

The preferred embodiments of the invention will now be described.

STRUCTURE

Figure 1:
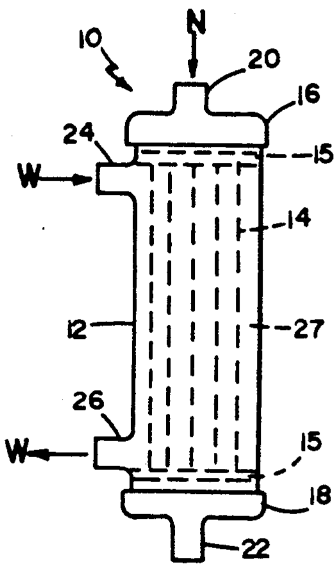
FIG. 1 is a diagrammatic elevation of a perfusion device according to the invention.

Referring to FIG. 1, there is shown perfusion device 10 including rigid, plastic outer shell 12, a plurality of hollow semipermeable membrane fibers 14 therein, and outer caps 16, 18. Fibers 14 thus are porous fibers. The upper and lower ends of hollow fibers 14 are potted in potting material 15 and thereby sealed to the inner surface of shell 12 near the upper and lower ends, employing techniques which are well known in the art. Cap 16 has perfusion inlet 20, and cap 18 has perfusion outlet 22, both of which communicate with the interiors of hollow fibers 14. Ports 24, 26 are inward of potting 15 and provide access to the region within container 12 external of hollow fibers 14. Fibers 14 act as a barrier between perfusion compartment 25, inside of the fibers (FIG. 2), and hepatocyte compartment 27, in the region between the exterior surfaces of fibers 14 and the inside of shell 12.

Figure 2:
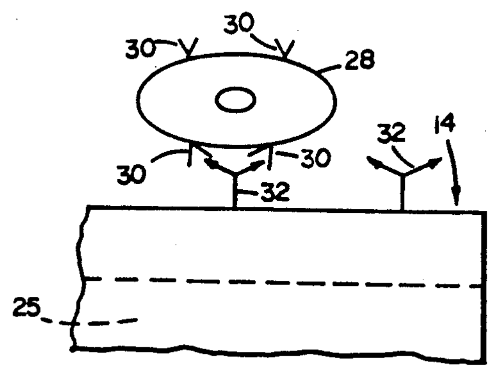
FIG. 2 is a diagrammatic representation showing attachment of a hepatocyte cell to an exterior surface of a hollow fiber of the FIG. 1 device.
Figure 3:
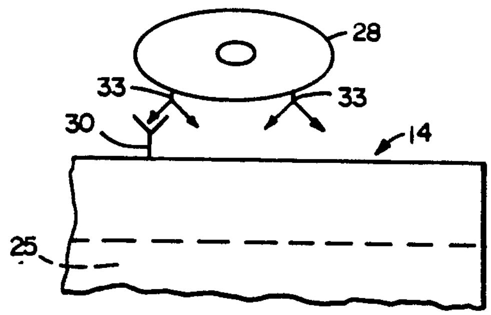
FIG. 3 is a diagrammatic representation of an alternative attachment of a hepatocyte cell to the external surface of a hollow fiber in the FIG. 1 device.

Referring to FIG. 2, there is shown a hepatocyte 28 that is attached to the external surface of hollow fiber 14 via an oligosaccharide-lectin recognition linkage including sugars 30, naturally present on the surface of hepatocyte 28, and lectins 32, covalently bound to hollow fiber 14. Lectins 32 preferably are Lens culinaris agglutinin (LCA, specific for α-D-mannosyl and α-D-glucosyl) or Phaseolus vulgaris agglutinin (PHA, specific for β-D-galactosyl-(1-3)-NAc-galoctosyl-β-D-galactosyl). Referring to FIG. 3, disclosing an alternative method of attachment, hepatocyte 28 is shown similarly attached to external surface of hollow fiber 14 via an oligosaccharide-lectin recognition linkage, but in this case sugar 30 (galactose) is covalently bound to fiber 14, and lectin 33 (asialoglycoprotein receptor) is one naturally existing on the surface of hepatocyte 28 (See Steer, C. J., et al., "Studies on a Mammalian Hepatic Binding Protein Specific for Asialoglycoproteins", *Journal of Biological Chemistry,* Vol. 255, No. 7, Apr. 10, 1980, pp. 3008-3013). An advantage of this arrangement is that only liver cells attach to the membrane.

Figure 4:
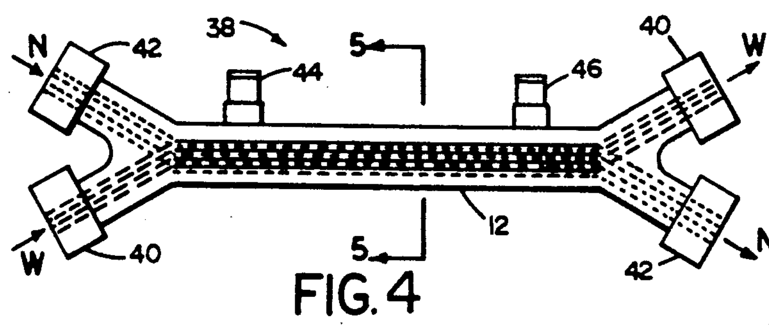
FIG. 4 is a diagrammatic elevation of an alternative embodiment of a perfusion device according to the invention.
Figure 5:
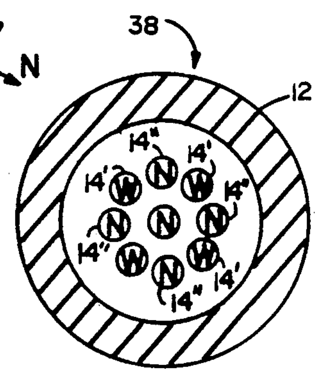
FIG. 5 is a diagrammatic vertical sectional view, taken at 5—5 of FIG. 4, of the FIG. 4 device.
Figure 6:
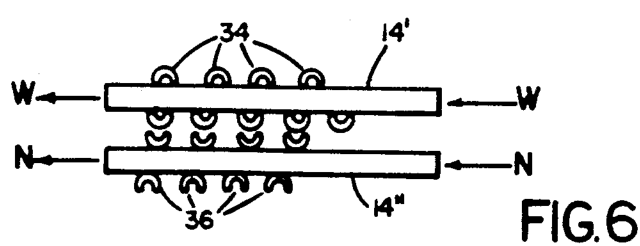
FIG. 6 is a diagrammatic representation of polarized attachment of hepatocytes to hollow fibers in the FIG. 4 alternative embodiment.

Referring to FIGS. 4–6, disclosing an alternative embodiment, perfusion device 38 includes hollow fibers 14' for a waste stream, W, and hollow fibers 14" for a nutrient stream, N. While concurrent flow is indicated in FIG. 4, counter-current flow can be used and may be preferred. Hollow fibers 14' are potted in waste ports 40 to provide a waste flow through passage inside of fibers 14', and hollow fibers 14" are potted in nutrient ports 42 to provide a nutrient flow-through passage inside of fibers 14". A further compartment is provided by the region inside of shell 12 and outside of fibers 14', 14"; this further compartment communicates with ports 44, 46. Referring to FIG. 6, hepatocytes 34 are attached to hollow fiber 14' via wheat germ agglutinin lectins, which recognize sugars located predominantly at the bile domain of hepatocytes 34 (namely β-N-acetylglucosamine and NAc-neuraminic acid). Hepatocytes 36 are attached to hollow fiber 14" via LCA or PHA lectins, which recognize sugars (listed above) located predominantly at the sinusoidal domain (blood pole). Thus the blood poles of hepatocytes 36 are directed to receive nutrients from nutrient stream N, and the bile poles of hepatocytes 34 are directed to excrete waste to waste stream W.

Manufacture and Use

Artificial liver 10 is made from a standard shell 12 provided with potted hollow fibers according to procedures that are well known in the art. Fibers 14 are made of polyacrylic polyurethane, have outer diameters between $150\mu$ and $400\mu$, have inner diameters between $50\mu$ and $350\mu$, have pores or a size to have MW cutoffs of 40,000 to 250,000. The outer surfaces of fibers 14 are treated to provide carboxy and/or amino groups to facilitate attachment of lectins by techniques known in the art. E.g., the outer fiber surfaces could be treated to provide hydroxyl groups, which are then used to generate carboxy and/or amino groups, according to well known techniques (Curtis, A. S. G., et al., "Substrate Hydroxlyation and Cell Adhesion", *J. Cell Science,* Vol. 86, 1986, pp. 9–24, Schnabel, W., *Polymer Degradation,* (Munich, 1981)). Lectins 32 are covalently bonded to the exterior surfaces of the hollow fibers using the carbodiimide method described in Hatten, M. E., and Francois, A. M., "Adhesive Specificity of Developing Cerebellar Cells on Lectin Substrata", *Developmental Biology,* Vol. 87, 1981, pp. 102–113. If the alternative attachment method of FIG. 3 is employed, sugars, and not lectins, are covalently bonded onto the outer surfaces of fibers 14.

Hepatocytes are prepared from human, rat, or pig livers and isolated by a modification of the method described in Seglen, P. O. "Preparation of Isolated Rat Liver Cells", Chapter 4, from *Methods in Cellular Biology,* 13:29–83 (1976), using Chee's modified essential tissue culture Medium (Scott Labs, Fiskeville, RI or MA Bioproducts, Walkersville, MD) with the addition of 10% fetal bovine serum. This tissue culture medium contains increased concentrations of arginine, asparagine, isoleucine, leucine, serine, valine, and glutamine. An increased buffering capacity is afforded by the inclusion of 5 mg/l sodium bicarbonate.

The seeding medium including hepatocytes is injected through ports 24, 26 into hepatocyte compartment 27, filling the region between the exteriors of the hollow fibers; ports 24, 26 are closed, and the seeding medium is retained in hepatocyte compartment 27 with air inside the fibers for two hours, while hepatocyte attachment takes place. Fresh medium (without hepatocytes) is flushed via ports 24, 26 through compartment 27, removing unattached cells within compartment 27 (e.g., 10 to 20% of cells). The seeding medium contains enough hepatocytes so that the number actually attached is at least $87 \times 10^9$ (a number of hepatocytes calculated to be able to maintain a human with total liver failure). Fresh medium (without hepatocytes) is also flushed through the interiors of the fibers at 15 ml per minute in order to maintain the cells. This medium is recycled through an endless loop that is made primarily of PTFE (chosen for low absorption characteristics); the loop also includes a small portion of Neoprene tubing in a peristaltic pump (chosen for relatively low absorption and good flexibility characteristics for the pump) and a one-meter long section of Tygon tubing (chosen for oxygen permeability, even though it has relatively high absorption characteristics).

The manufacture of device 38 is similar, the different lectins being attached to respective fibers 14', 14".

The time between cell attachment and use could, e.g., be between 24 hours and four weeks. During this period, the medium is continuously perfused through the fiber interiors as noted above in order to maintain the cells, providing them with nutrients and oxygen.

Perfusion device 12 can be used as a hepatocyte reactor to study the effect of different conditions (e.g., different toxics and nutrients) on the functioning of hepatocytes.

Figure 7:
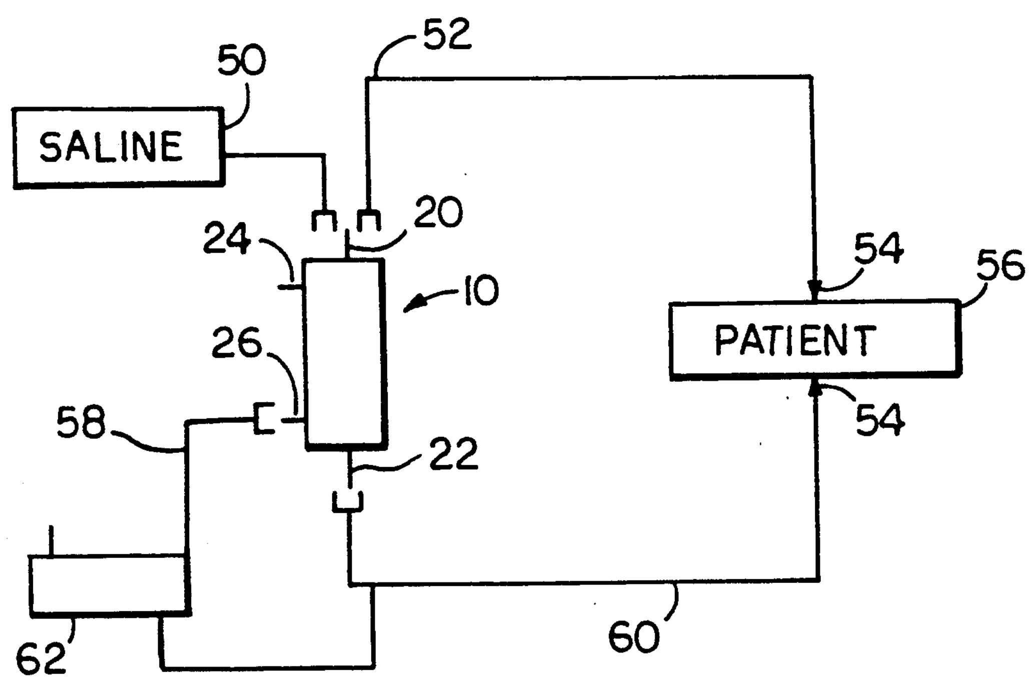
FIG. 7 is a flow diagram showing the FIG. 1 device in use connected to a patient.

Another use for perfusion device 12 is as an artificial liver for a patient awaiting a liver transplant, referring to FIG. 7, the nutrient medium is first flushed from the fiber interiors using sterile saline solution 50. Perfusion inlets and outlets 20, 22 are connected, maintaining sterile conditions, to a sterile tubing set 52 having removal and return venipuncture needles 54 for connection to a patient 56. The tubing set could also include connections for further extracorporeal blood treatment, e.g., dialysis or a procedure involving blood component separation, e.g., plasma exchange. Port 26 could be connected to a flow path 58 providing for removal of waste products of hepatocytes in hepatocyte compartment 27 and possible selective return of some components in compartment 27 to the blood flow line 60 to the patient, e.g., using a further ultrafiltration membrane device 62 to limit size of components returned to the patient's blood.

After the entire tubing set has been primed with sterile saline, it is connected via its venipuncture needles to the patient, and blood flows through the interior of fibers 14. Toxic chemicals and other entities in the blood that are smaller than the pore size and have a higher concentration in compartment 25 than the liquid in hepatocyte compartment 27 pass through the semipermeable membrane wall of fiber 14 and are metabolized by hepatocytes 28. Larger components of the blood, e.g., white and red cells and immunoglobulins, do not pass through the pores. The blood in fibers 14 is at a higher pressure than that in hepatocyte chamber 27, and this transmembrane pressure additionally causes ultrafiltration.

The use of perfusion device 38 is similar, with further possibilities being provided for waste processing by the additional waste fibers 14' and waste ports 40.

Hepatocytes 28 maintain their cytochrome P-450 function and thus are able to detoxify many toxic components responsible for the syndrome of hepatic encephalopathy. Hepatocytes 28 similarly maintain chemical production functions, and chemicals produced by them can be returned to the patient by two possible paths: through the membrane wall of fiber 14 or via a further ultrafiltration membrane device connected to port 26, as noted above.

Experiments have demonstrated that hepatocytes attached to the exterior surfaces of hollow semipermeable membranes via oligosaccharide-lectin recognition linkage have been viable and have maintained the glucuronidation on function of hepatocytes, as determined by metabolism of phenol red. Experiments have also demonstrated that hepatocytes attached to the exterior surface of hollow fibers via oligosaccharide-lectin recognition linkage have maintained cytochrome P-450 activity.

Other Embodiments

Other embodiments of the invention are within the scope of the following claims. For example, other lectins that attach hepatocytes to membranes could be used, e.g., the lectins noted in McMillan, P. N., "Light and Electron Microscope Analysis of Lectin Binding to Adult Rat Liver In Situ", *Laboratory Investigation*, Vol 50, No. 4 (1984) pp. 408–470, which is hereby incorporated by reference along with the other references referred to herein. Specific lectins that can be used in the oligosaccharide-lectin recognition linkage according to the invention are Concanavalin A (Con A, specific for α-D-mannose, α-D-glucose, and α-NAc-glucosamine), Ricinus communis agglutinin (RCA I, specific for β-D-galactose and α-D-galactose), and Pisum sativum agglutinin (PSA, specific for α-D-mannose, α-D-glucose).

What is claimed is:

1. An article of manufacture to grow and maintain hepatocytes comprising:

a chamber having a perfusion inlet means and a perfusion outlet means, a porous membrane means mounted in and secured to said chamber so as to define a perfusion compartment and an adjacent, separate hepatocyte compartment in said chamber, said perfusion inlet means and said perfusion outlet means being in fluid communication with said perfusion compartment, said membrane means being made of a biocompatible polymer, at least one of a first oligosaccharide and a first lectin fixedly attached to a portion of said membrane means facing said hepatocyte compartment, and first hepatocytes attached to said at least one of a first oligosaccharide and a first lectin via oligosaccharide-lectin recognition linkages.

2. The article of claim 1, wherein said first hepatocytes have cytochrome P450 activity.

3. The article of claim 1, wherein said membrane means comprises a first set of porous hollow fibers, the interiors of said hollow fibers defining said perfusion compartment.

4. The article of claim 1, wherein said at least one of a first oligosaccharide and a first lectin is a first lectin and is fixedly attached by covalent bonding.

5. The article of claim 1, wherein said at least one of a first oligosaccharide and a first lectin is a first oligosaccharide and is fixedly attached by covalent bonding.

6. The article of claim 4, wherein said first lectin is a member selected from the group consisting of Ricinus communis agglutinin, wheat germ agglutinin, Pisum sativum agglutinin, Lens culinaris agglutinin, Phaseolus vulgaris agglutinin, and Concanavalin A.

7. The article of claim 6, wherein said first lectin is Lens culinaris agglutinin.

8. The article of claim 6, wherein said first lectin is wheat germ agglutinin.

9. The article of claim 3, wherein said first set of hollow fibers are made of polyacrylic polyurethane.

10. The article of claim 3, wherein said chamber further comprises a waste inlet means and a waste outlet means and wherein said membrane means further comprises a second set of hollow fibers, wherein the interiors of said second set of hollow fibers define a separate waste compartment adjacent said hepatocyte compartment, said waste inlet means and said waste outlet means being in fluid communication with said waste compartment.

11. The article of claim 10, wherein said at least one of a first oligosaccharide and a first lectin is attached to the exterior of said first set of hollow fibers and further comprising, at least one of a second oligosaccharide and a second lectin fixedly attached to the exterior of said second set of hollow fibers and second hepatocytes attached to said at least one of a second oligosaccharide and a second lectin via oligosaccharide-lectin recognition linkages.

12. The article of claim 11, wherein said at least one of a first oligosaccharide and a first lectin is a first lectin, said first lectin recognizing sugars located predominantly at the sinusoidal domain of said first hepatocytes.

13. The article of claim 12, wherein said at least one of a second oligosaccharide and a second lectin is a second lectin, said second lectin recognizing sugars located predominantly at the bile domain of said second hepatocytes.

14. The article of claim 13, wherein said first lectin is a member of the group consisting of Lens culinaris agglutinin or Phaseolus vulgaris agglutinin.

15. The article of claim 14, wherein said second lectin is wheat germ agglutinin.

16. The article of claim 3, 6, 9 or 11, wherein said first hepatocytes have cytochrome P450 activity.

17. The article of claim 1, further comprising tubes for connection to a patient, said tubes being connected to said perfusion inlet means and said perfusion outlet means.

18. The article of claim 17, further comprising returning means for returning some products produced by said hepatocytes to the patient.

19. The article of claim 18, further comprising treating means for treating the products prior to return to the patient.

20. The article of claim 1, further comprising flushing means for flushing nutrients through said perfusion compartment.

21. The article of claim 1, wherein said membrane means has molecular weight cutoffs of 40,000 to 250,000.

22. The article of claim 1, wherein said membrane means is constructed so as to prevent passage of white and red cells and immunoglobulins therethrough.

23. An article of manufacture to grow and maintain hepatocytes comprising:

a chamber having a perfusion inlet means and a perfusion outlet means, a porous membrane means mounted in and secured to said chamber so as to define a perfusion compartment and an adjacent, separate hepatocyte compartment in said chamber, said perfusion inlet means and said perfusion outlet means being fluid communication with said perfusion compartment, said membrane means being made of a biocompatible polymer, a biocompatible polymer support means in said hepatocyte compartment, at least one of a first oligosaccharide and a first lectin fixedly attached to a portion of at least one of said support means and said membrane means facing said hepatocyte compartment, and first hepatocytes attached to said at least one of a first oligosaccharide and first lectin via oligosaccharide-lectin recognition linkages.

24. The article of claim 23, wherein said first hepatocytes have cytochrome P450 activity.

25. The article of claim 23, wherein said at least one of a first oligosaccharide and a first lectin is a first lectin and is fixedly attached by covalent bonding.

26. The article of claim 25, wherein said first lectin is a member selected from the group consisting of Ricinus communis agglutinin, wheat germ agglutinin, Pisum sativum agglutinin, Lens culinaris agglutinin, Phaseolus vulgaris agglutinin, and Concanavalin A.

27. A method of making a perfusion device for growing and maintaining hepatocytes comprising:

providing a chamber having a perfusion inlet means and a perfusion outlet means, a porous membrane means mounted in and secured to said chamber so as to define a perfusion compartment and an adjacent, separate hepatocyte compartment in said chamber, said perfusion inlet means and said perfusion outlet means being in fluid communication with said perfusion compartment, said membrane means being made of a biocompatible polymer, fixedly attaching at least one of a first oligosaccharide and a first lectin to a portion of said membrane means facing said hepatocyte compartment, and attaching first hepatocytes to said at least one of a first oligosaccharide and a first lectin via oligosaccharide-lectin recognition linkages.

28. The method of claim 27, wherein said first hepatocytes have cytochrome P450 activity.

29. The method of claim 27, wherein said membrane means comprises a first set of porous hollow fibers, the interiors of said hollow fibers defining said perfusion compartment.

30. The method of claim 29, wherein said at least one of a first oligosaccharide and a first lectin is a first lectin and said first lectin is fixedly attached by covalent bonding.

31. The method of claim 30, wherein said first lectin is a member selected from the group consisting of Ricinus communis agglutinin, wheat germ agglutinin, Pisum sativum agglutinin, Lens culinaris agglutinin, Phaseolus vulgaris agglutinin, and Concanavalin A.

32. The method of claim 30, wherein said first hepatocytes are attached by injecting a seeding medium including said first hepatocytes into said hepatocyte compartment.

33. The method of claim 32, which further comprises waiting a period of time after said injecting to allow said first hepatocytes to attach to said first lectin, and then flushing said medium from said hepatocyte compartment.

34. The method of claim 33, further comprising flushing nutrients through said perfusion compartment after attaching said first hepatocytes to maintain said first hepatocytes.

35. A method of making a perfusion device for growing and maintaining hepatocytes comprising:

providing a chamber having a perfusion inlet means and a perfusion outlet means, a porous membrane means mounted in and secured to said chamber so as to define a perfusion compartment and an adjacent, separate hepatocyte compartment in said chamber, a biocompatible polymer support means in said hepatocyte compartment, said perfusion inlet means and said perfusion outlet means being in fluid communication with said perfusion compartment, said membrane means being made of a biocompatible polymer, fixedly attaching at least one of a first oligosaccharide and a first lectin to a portion of at least one of said support means and said membrane means facing said hepatocyte compartment, and attaching first hepatocytes to said at least one of a first oligosaccharide and a first lectin via oligosaccharide-lectin recognition linkages.

36. The method of claim 35, wherein said first hepatocytes have cytochrome P450 activity.

37. The method of claim 35, wherein said at least one of a first oligosaccharide and a first lectin is a first lectin and said first lectin is fixedly attached by covalent binding.

38. The method of claim 37, wherein said first lectin is a member selected from the group consisting of Ricinus communis agglutinin, wheat germ agglutinin, Pisum sativum agglutinin, Lens culinaris agglutinin, Phaseolus vulgaris agglutinin, and Concanavalin A.

39. A method of using a hepatocyte perfusion device comprising:

providing a perfusion device including a chamber having a perfusion inlet means and a perfusion outlet means, a porous membrane means mounted in and secured to said chamber so as to define a perfusion compartment and an adjacent, separate hepatocyte compartment in said chamber, said perfusion inlet means and said perfusion outlet means being in fluid communication with said perfusion compartment, said membrane means being made of a biocompatible polymer, at least one of a first oligosaccharide and a first lectin fixedly attached to a portion of said membrane means facing said hepatocyte compartment, and first hepatocytes attached to said at least one of a first oligosaccharide and a first lectin via oligosaccharide-lectin recognition linkages, and causing perfusion liquid to flush through said inlet means, said perfusion compartment, and said outlet means.

40. The method of claim 39, wherein said first hepatocytes have cytochrome P450 activity.

41. The method of claim 39, wherein said membrane means comprises a first set of porous hollow fibers, the interiors of said hollow fibers defining said perfusion compartment.

42. The method of claim 41, wherein said first lectin is a member selected from the group consisting of Ricinus communis agglutinin, wheat germ agglutinin, Pisum sativum agglutinin, Lens culinaris agglutinin, Phaseolus vulgaris agglutinin, and Concanvalin A.

43. The method of claim 40, wherein said perfusion liquid comprises blood, and tubes connect a patient to said perfusion inlet means and outlet means.

44. The method of claim 43, further comprising returning some products produced by said first hepatocytes to the patient.

45. The method of claim 44, further comprising treating said products prior to return to said patient.

46. The method of claim 39, further comprising flushing nutrients through said perfusion compartment.

47. A method of using a hepatocyte perfusion device comprising:

providing a perfusion device including a chamber having a perfusion inlet means and a perfusion outlet means, a porous membrane means mounted in and secured to said chamber so as to define a perfusion compartment and an adjacent, separate hepatocyte compartment in said chamber, biocompatible polymer support means in said hepatocyte compartment, said perfusion inlet means and said perfusion outlet means being in fluid communication with said perfusion compartment, said membrane means being made of a biocompatible polymer, at least one of a first oligosaccharide and a first lectin fixedly attached to a portion of at least one of said support means and said membrane means facing said hepatocyte compartment, and first hepatocytes attached to said at least one of a first oligosaccharide and a first lectin via oligosaccharide-lectin recognition linkages, and causing perfusion liquid to flush through said inlet means, said perfusion compartment, and said outlet means.

48. The method of claim 47, wherein said first hepatocytes have cytochrome P450 activity.

49. The method of claim 41, wherein said first lectin is a member selected from the group consisting of Ricinus communis agglutinin, wheat germ agglutinin, Pisum sativum agglutinin, Lens culinaris agglutinin, Phaseolus vulgaris agglutinin, and Concanavalin A.

* * * * *